(12) United States Patent
Friedlaender et al.

(10) Patent No.: US 8,394,866 B2
(45) Date of Patent: Mar. 12, 2013

(54) METHOD AND DEVICE FOR THE DECONTAMINATION OF PLASTIC FLAKES

(75) Inventors: Thomas Friedlaender, Regensburg (DE); Thomas Rieckmann, Kaufungen (DE); Frank Marx, Bornheim (DE)

(73) Assignee: Krones AG, Neutraubling (DE)

( * ) Notice: Subject to any disclaimer, the term of this patent is extended or adjusted under 35 U.S.C. 154(b) by 620 days.

(21) Appl. No.: 11/886,986

(22) PCT Filed: Mar. 15, 2006

(86) PCT No.: PCT/EP2006/002356
§ 371 (c)(1),
(2), (4) Date: Feb. 16, 2009

(87) PCT Pub. No.: WO2006/099976
PCT Pub. Date: Sep. 28, 2006

(65) Prior Publication Data
US 2009/0192235 A1  Jul. 30, 2009

(30) Foreign Application Priority Data
Mar. 24, 2005 (DE) .......................... 10 2005 013 701

(51) Int. Cl.
*C08J 11/04* (2006.01)
(52) U.S. Cl. ............ 521/40; 521/40.5; 521/41; 521/46; 521/47; 521/48; 521/49; 528/308.2; 528/308.5; 528/480; 528/501; 528/502 R; 528/502 C; 528/502 F; 528/503; 422/134; 422/138; 422/245.1; 422/273; 422/307
(58) Field of Classification Search .......... 521/40, 521/40.5, 41, 45.5, 46, 48, 49.8; 528/271, 528/272, 308.1, 308.2, 308.3, 308.5, 308.6, 528/480, 481, 501, 502 R, 502 F, 503; 131, 422/134, 138, 145, 146, 245.1, 273, 305, 422/307, 308
See application file for complete search history.

(56) References Cited

U.S. PATENT DOCUMENTS
4,370,302 A    1/1983 Suzuoka et al.
(Continued)

FOREIGN PATENT DOCUMENTS
| CA | 2 284 965 A1 | 5/2000 |
| DE | 19953659 | 5/2001 |
| DE | 103 24 098 A1 | 12/2004 |
| EP | 0856537 | 8/1998 |
(Continued)

OTHER PUBLICATIONS

Culbert et al., "Continuous Solid-State Polycondensation of Polyesters," Modern Polyesters: Chemistry and Technology of Polyesters and Copolyesters, pp. 143-194 (2003).
(Continued)

*Primary Examiner* — Frances Tischler
(74) *Attorney, Agent, or Firm* — Marshall, Gerstein & Borun LLP

(57) ABSTRACT

A method for preparing contaminated plastics ground into flakes, such as RPET or such polymers, having at least decontamination and SSP treatment steps, with at least one reactor, with heating to the process temperature taking place essentially outside the reactor. Also, a device for carrying out the method, and having at least one decontamination reactor and at least one SSP reactor, a device for heating plastic flakes to the process temperature being arranged upstream of the decontamination reactor. Also an SSP reactor having at least two individual reactors, and preferably between 3 and 7 individual reactors.

29 Claims, 2 Drawing Sheets

U.S. PATENT DOCUMENTS

| | | | |
|---|---|---|---|
| 6,066,713 A * | 5/2000 | Mrose et al. | 528/272 |
| 6,730,774 B1 * | 5/2004 | Christel et al. | 528/500 |
| 2001/0004645 A1 | 6/2001 | Robinson et al. | |
| 2002/0026030 A1 * | 2/2002 | Duh | 528/272 |
| 2006/0093533 A1 * | 5/2006 | Fellinger et al. | 422/131 |

FOREIGN PATENT DOCUMENTS

| | | |
|---|---|---|
| WO | WO-0046004 | 8/2000 |
| WO | WO-01/21372 A1 | 3/2001 |
| WO | WO-01/21373 A1 | 3/2001 |
| WO | WO-03/037588 A1 | 5/2003 |
| WO | WO 2004/029130 A1 * | 4/2004 |
| WO | WO-2005037513 | 4/2005 |
| WO | WO-2005121230 | 12/2005 |

OTHER PUBLICATIONS

Fellinger, "Solid State Polycondensation of PET for Recycling Applications with Food Contact," Session 9b presentation at Pet Process Advances (Dec. 2004).

Objection Against European Patent No. 1 861 455, dated Jul. 7, 2009.
Objection to European Patent No. 1 861 455, dated Dec. 16, 2009.
Objection to European Patent No. 1 861 455, dated May 19, 2010.
Objection to European Patent No. 1 861 455, dated Dec. 22, 2010.
Objection to European Patent No. 1 861 455, dated Dec. 23, 2011.
Objection Against European Patent No. 1 861 455, dated Jan. 30, 2012.

* cited by examiner

METHOD AND DEVICE FOR THE DECONTAMINATION OF PLASTIC FLAKES

CROSS-REFERENCE TO RELATED APPLICATION

The present application claims the benefit of priority of International Patent Application No. PCT/EP2006002356 filed on Mar. 15, 2006, which application claims priority of German Patent Application No. 10 2005 013 701.6 filed Mar. 24, 2005. The entire text of the priority application is incorporated herein by reference in its entirety.

FIELD OF THE DISCLOSURE

The disclosure relates to a method for preparing contaminated plastics ground into flakes, to a device for carrying out the method, and to a reactor unit for carrying out an SSP (solid state polycondensation) treatment.

BACKGROUND

Consumer items made of plastic are used increasingly, for example, beverage bottles made of PET, household objects, such as, keys or similar items, or housing parts of electronic apparatuses. The worldwide spread of plastics in the greatest variety of fields has, in the meantime, reached such proportions that the raw materials are becoming rarer and thus more expensive. Recycling plastics is important not only for environmental reasons, it is also becoming more advantageous from an economic standpoint.

As raw material prices increase, the recycling methods that are of greatest interest are those that either maintain or increase the quality of the original material with regard to processability after recycling.

Originally, the assumption was that collected PET material (RPET), owing to the quality loss after recycling and different contaminations, could no longer be used in the same application (for example, beverage bottles). However, it has recently become apparent that such a use is possible. Methods exist which recycle the plastics at a qualitatively high level, to allow their reuse in the same application (for example, the food sector).

Using a method according to DE 199 53 659 A1, post-consumer PET bottles (RPET) are crushed, and first washed and surface dried in the usual way. Then the flakes are introduced into a crystallizer, in which they are heated and crystallized by a hot gas stream at 180° C. Then, the flakes reach a shaft reactor, where they are recondensed continuously for at least two hours in countercurrent flow with respect to an N2 gas stream (temperature approximately 220° C.). Then the flakes are cooled again in this continuously running process. One drawback of this method is that the PET flakes are heated in the given reactors, i.e., in the crystallizer and the shaft reactor, respectively, which requires a relatively large amount of heating energy. In addition, the heat transfer is carried out via (inert) gas, which requires a complicated preparation system for the heat transfer medium. Another disadvantage of the method is that the recondensation of the flakes is continuous. In a continuous process management, the desired IV (intrinsic viscosity) cannot be set exactly, because the heating which can be carried out is limited by process parameters (for example, temperature and time). The fact that the actual IV of the flakes to be treated can be different—for example, some flakes have an intrinsic viscosity IV of 0.70 dL/g, while others already have a value of 0.76 dL/g—is not taken into account in this procedure, so that all the flakes undergo an increase in their intrinsic viscosity in the same way (same time, same process conditions), without taking into account their original IV.

Therefore, the problem of the present disclosure is to provide a method and a device for recycling plastics, which present considerably reduced energy consumption, and in which the IV of the plastics can be set in a controlled manner.

SUMMARY OF THE DISCLOSURE

The disclosure is based on the realization that the contaminants are not distributed evenly over the RPET, and that they are found primarily on the surface, or in surface-near areas. Therefore, a decontamination and/or SSP treatment are(is) sufficient to clean RPET so it becomes suitable for use with foods, and can be used again as packaging material for foods, for example, for beverage bottles. In addition, the disclosure is based on the surprising realization that RPET, in contrast to new (virgin) PET, is not adhesive in the warn state, which, in the first place, allows for unproblematic processes in the processing technology (for example, the heating of RPET in a heating installation). The reason for this is that the RPET flakes contract in a surprising manner during the heating, which results in an increase of their thickness or their characterizing length. At the same time, a structured surface is produced, which reduces the contact surface area between the flakes.

In principle, the size of the flakes plays no role insofar as the feasibility of the method is concerned. The only factor that changes with increasing particle size is the residence time in the reactors. The larger the average particle size is, the longer the residence time in the reactor is as well. Therefore, it is also conceivable not to reduce the size of the plastic objects before their treatment, or to reduce it only slightly. Thus, flakes are defined as any objects that, in their shape and size, no longer correspond to their original application form. However, as a general rule, the flakes present an average particle size ranging from a few millimeters to a few centimeters.

The prepping of the flakes before the preparation, i.e., the cleaning and the crushing, is usually carried out in larger collection centers; however, it is also conceivable to carry out the crushing and (coarse) cleaning of the flakes onsite, immediately before the preparation.

Preparation here denotes not only the surface cleaning or decontamination of the flakes, but also the improvement or reconstitution of the physical and of the chemical properties of the flakes, to ensure a renewed high-value use (for example, in the stretch blow molding of beverage bottles), particularly for the packaging of, for example, liquid foods that come in direct contact with the plastic.

Because the method can be transposed to the large industrial scale and also to small installations, the reactors are larger boilers, containers, etc., and also smaller containers, which can be substantially closed off from the environment.

The heating of the flakes to be treated to the process temperature is carried out according to the disclosure substantially in a treatment unit, which is outside of the reactor. This heating can be either a continuous heating or a batch-wise heating of the flakes. In the reactor itself, the flakes are barely heated, or no longer heated, but merely maintained at a process temperature, or heat losses are compensated. Thus, the process control is substantially adiabatic.

SSP (solid state polycondensation) denotes the process of molecular chain elongation of plastics in the solid phase. The SSP process is a standard process, which every person skilled in the art of the field of PET plastic technology knows. The term SSP treatment here can also denote a negative molecular chain elongation, that is a depolymerization, or a treatment in which the molecular chains on average remain substantially the same. Regardless of whether the molecular chains are shortened, lengthened, or remain the same, an additional decontamination of the flake occurs during the SSP process due to the process conditions (including temperature, time).

It is particularly advantageous to use a process control where both decontamination and the SSP treatment occur each in a separate reactor. The two reactors can thus be regulated independently of each other at the same time with respect to their reaction conditions (pressure, temperature, gas type).

It is preferred for both reactors to be under adiabatic conditions. It is conceivable for the small heat losses of the flakes to be compensated in the reactor by a reactor heating. For this purpose, any heating type can be used (for example, water, steam, electrical, heat carrier oil, such as, thermal oil).

According to a particularly preferred embodiment, the material to be prepared in the reactors is not set into motion, mechanically, pneumatically, or in any other way. As a result, during the process of the decontamination and the SSP treatment, respectively, the flakes cannot become statically charged due to mutual friction or interaction with the reactor walls, and also, no abrasion products build up, which would increase the difficulty or the complexity of continuing the process, or even make it impossible to carry out the process.

To remove the contaminants, a hot gas flows around the flakes during the decontamination step. The hot gas is preferably air, to ensure that the process control is as simple as possible. In the decontamination reactor, the temperature in the decontamination reactor here is 20-200° C., preferably 100-180° C., and most advantageously 150-170° C. The functional capability of the process is ensured at all the indicated temperatures; only the residence time in the reactor changes. The higher the temperature in the decontamination reactor is, the lower the residence time is. The optimal operational point of the decontamination reactor with respect to temperature is therefore 150-170° C., because, on the one hand, the temperature is relatively high and thus the residence time in the reactor is relatively short, and, on the other hand, air can be used as gas for removing the contaminants. At temperatures above approximately 180° C., air can no longer be used as hot gas, because it would enter into different reactions with the material. In this case, one would have to use nitrogen, for example. The process of the decontamination can also be carried out at a temperature below 20° C.; however, the residence time in the reactor then becomes very long. The gas has a temperature which corresponds substantially to that of the decontamination process. As a result, heat losses of the flakes can be compensated.

With regard to heating the flakes to the process temperature, it is possible to carry out the heating in a batch process or continuously. It is preferred to carry out the heating continuously, as close as possible to the decontamination reactor. The closer the heating unit is to the decontamination reactor, the less abrasion products form during the transport. The better the heat transfer from the heating unit to the flakes, the more energy can be saved in the heating process. To heat the flakes continuously before the decontamination, it is preferred to use a heating screw or a vibrating helical conveyor. Other heating units are also conceivable, however, the heating screw and the vibrating helical conveyor present the advantage of a good heat transfer to the flakes. It is preferred to use thermal oil as the heat carrying medium in the heating screw, where, for example, the heating can also be carried out with steam, with hot water, or electrically.

In a preferred embodiment, the SSP process is carried out at low-pressure conditions. Although it is also possible to allow the process to take place under atmospheric conditions or excess pressure conditions, the vacuum offers the advantage that the substance transfer of volatile compounds from the flakes to the gas phase is improved, and thus the contaminants can be removed better, and the conditions for molecular chain elongation are also more advantageous. The vacuum which is used for the SSP process should optimally present a gas pressure of at most 100 millibar, preferably 10-0.1 millibar. If the SSP process is carried out under atmospheric conditions or excess pressure conditions, then one must ensure that there is sufficient flow around the particles, to improve the substance transfer, or to be able to remove the contaminants better.

In a preferred embodiment, the temperatures in the SSP reactor for adjusting the IV are higher than in the decontamination reactor. The temperature here preferably has at least the value of the temperature in the decontamination reactor, and at most the value of the melting temperature of the flakes to be treated. The temperature here is advantageously 150-250° C., and particularly advantageously 170-210° C.

The increase the process temperature, from the temperature of the decontamination reactor to that of the SSP reactor, is carried out preferably in a separate heat transfer device located between the two reactors. It is preferred for the heat transfer device to be again a heat exchanger, or a heating installation, which uses thermal oil as the heat transfer medium. According to a particularly preferred variant, the heat transferring device is a heating screw or a vibrating helical conveyor. The use of a hot air conveyor, an infrared tunnel, or a similar device is also conceivable.

Special advantages in carrying the SSP process can be achieved by conducting the process under an inert gas atmosphere. If nitrogen or carbon dioxide is used as protective gas, the process can be carried out particularly well. Additional advantages arise from the use of the gas stream which removes degradation products, contaminants, ultrafine particles or similar substances from the reactor. The gas in which the SSP process occurs is preferably atmospheric gas. The gas stream here as well is preferably not too strong, so that the gas flakes are not moved. The only purpose of the gas stream is to ensure the removal of the degradation products.

To optimize the process with regard to the regulation of the IV of the flake, the current value of the intrinsic viscosity is determined at least once during the preparation process. However, it is particularly preferred to use the procedure in which the IV is measured at least twice, where the results of the measurements determine the further course of the process, for example, the residence time or the temperature course.

In this context, it is particularly preferred to use a method in which the IV is determined spatially and/or temporally before the entrance of the material to be prepared into the SSP reactor. Based on this value, with a fixed temperature, the residence time in the SSP reactor can be determined. After half of the calculated residence time has elapsed, another measurement of the IV is carried out, and based on this result the residence time remaining is controlled and corrected if necessary. The measurement of the IV of the flakes can be carried out either in the reactor or outside of the reactor, where the sample collection is carried out by means of a flake sampling device.

However, it is also conceivable to use a method in which a measurement of the IV is carried out, and to use this result to establish the temperature of the SSP process, the residence time being fixed. After half of the fixed residence time has elapsed, a measurement of the IV can be carried out again, where, based on the results, the temperature for the process time is controlled and corrected if necessary. In this variant of the method, the IV can also be measured analogously to the above embodiment, either inside or outside.

If the measurement of the intrinsic viscosity yields the desired result already before the SSP treatment, then the process is regulated so that the IV no longer changes. This can be done, for example, by an appropriate regulation of the humidity content of the flake, which, on average, compensates for molecular chain shortening by hydrolysis, and for molecular chain elongation by polycondensation. As a result, the overall value of the intrinsic viscosity remains the same.

If the measurement of the intrinsic viscosity before the SSP treatment yields an excessively high IV, a "negative" SSP treatment, i.e., a controlled depolymerization, is carried out, by an appropriate adjustment of the humidity content of the flakes so that molecular chain shortening by hydrolysis prevails over molecule elongation by polycondensation. The result is a lower IV.

If the regulation of the IV in the SSP reactor is completed, then a cooling of the flakes to a temperature of 50-100° C., or, in a preferred embodiment, to below 70° C., can be carried out. The cooling is carried out preferably in a cooling screw, a vibrating helical conveyor, or in a fluidized bed reactor, although other cooling devices can also be provided. If the cooling is carried out by means of a cold gas stream, then it is preferred to use environmental air, which ensures that the cooling process is simple. During the cooling of the environmental air, one must ensure that the total cooling process does not last too long and, particularly, that the cooling in the temperature range from the reaction temperature to 150° C. occurs very rapidly, preferably within one to three minutes. If cooling at this speed is impossible, a protective gas, preferably nitrogen or carbon dioxide, can be used, in the case of the gaseous cooling medium. The use of another cooling medium, such as, for example, a cooling liquid is equally possible.

The device for carrying out the method according to the disclosure presents at least two reactors, of which one is preferably a decontamination reactor and one an SSP reactor for the regulation of the IV. In the reactors, any desired plastic flakes can be prepared, but it is preferred to use PET flakes.

The device for heating the flakes, which is preferably a heating screw or a vibrating helical conveyor, is connected before the decontamination reactor. The purpose of the heating installation is to heat the flakes to the process temperature, before they enter into the treatment reactor. The heat transfer in the heat exchanger or in the heating installation can be designed much more efficiently than the heat transfer during the heating of the flakes in the reactor itself.

According to a particularly preferred variant, the decontamination reactor presents a conical shape, which broadens in the direction of gravity. This reactor design has the advantage that the heated flakes, which tend to form bridges, are prevented from doing so. Furthermore, it is possible for the reactor to present a heating installation which, although it does not heat the flakes, maintains their temperature, and thus compensates for heat losses.

According to a variant of the disclosure, at least two decontamination reactors are provided, which present preferably a gas through-flow device, to be able to remove the contaminants from the reactor. A gas through-flow device can also be provided for both reactors. As a result of the arrangement of two reactors, it is possible, for example, to treat different flakes in different reactors. This can become necessary, for example, if both thinner "trunk flakes" or wall flakes, and also thinner "neck flakes" of beverage bottles are to be processed.

Because the flakes have different characteristic lengths, they are introduced into two different reactors with different process parameters. An additional heating installation is provided between the decontamination reactor and the SSP reactor.

During the operation of the decontamination reactor, the filling height and the residence time of the flakes are preferably nearly constant. In addition, the operation of the reactor is preferably continuous, so that at all times exactly as many flakes are supplied as are removed after the decontamination.

The SSP reactor as well presents preferably a gas through-flow device which is capable of removing the contaminants. Because the temperature in the SSP reactor is preferably 170-210° C., the gas through-flow device is an inert gas feed, preferably with nitrogen or carbon dioxide, because otherwise there is the risk that the components of air, at these high temperatures, will initiate an oxidation process whose consequences may include an undesired yellow coloration of the product.

In a preferred embodiment, the SSP reactor presents a pump for the generation of the vacuum and a pump for the removal of the contaminants. According to a particularly preferred variant, only a pump is present, which ensures both the generation of the vacuum and the removal of the contaminants in the gas stream.

A cooling unit, which lowers the temperature of the flakes from that of the SSP process to a temperature below the glass transition point, is connected after the SSP reactor.

According to a particularly preferred embodiment of the disclosure, at least two reactors, preferably 3-7 individual reactors, are available to ensure a near continuous process for the SSP treatment. The arrangement with several reactors allows the batch-wise (interruption-free) process of regulating the IV through different reactors, in such a way that the cooling device, which is connected after the SSP reactor unit, is supplied continuously with hot flakes from the individual reactors of the reactor unit.

The SSP reactor unit presents preferably a flake distributor which supplies the different individual reactors successively. The individual reactors of the SSP reactor unit are preferably arranged in a substantially circular structure, to have as compact as possible a construction.

In spite of the fact that the SSP process is run in the batch mode, this multipart reactor arrangement can achieve a nearly continuous process. In this way, the advantages of a continuously running overall process (for example, the heating and cooling devices can be operated continuously) can be combined with the advantages of the batch-wise SSP process (for example, the IV can be regulated more precisely as a result of the batch-wise processing).

According to a second embodiment, there are both at least two decontamination reactors and also at least two SSP reactors.

The treatment times in the decontamination reactor and in the SSP reactor are a function of the initial IV and of the characteristic length, or of the particle size, of the flakes. They fall in the range from 20 min to 5 hours, preferably 45 min to 2 hours, and particularly advantageously 1 to 1.5 hours.

BRIEF DESCRIPTION OF THE DRAWINGS

An embodiment of the device and of the method, respectively, is explained in further detail with reference to the drawing. In the drawing.

DETAILED DESCRIPTION

Figure 1:
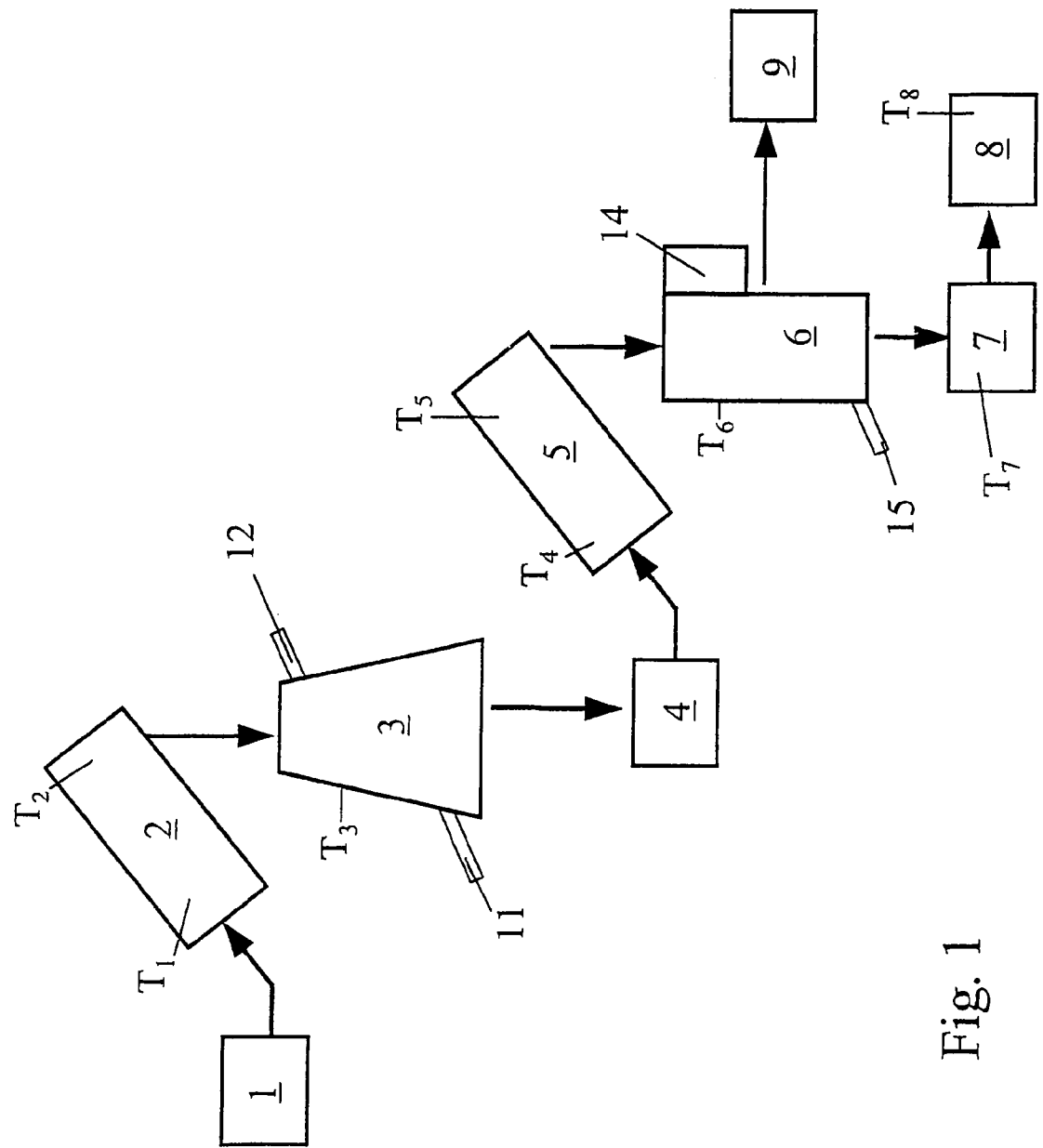
FIG. 1 shows a schematic representation of a process flow-chart.

In FIG. 1, a flake metering device 1 is shown, by means of which the flakes are conveyed in a predetermined manner into the decontamination heating screw 2. During the addition into the flake metering device 1, the flakes are washed, and their residual humidity is less than 3%. At the beginning of the transport of the flakes through the decontamination heating screw 2, they are at room temperature T1. (Flakes from previous processes may also still retain residual heat.) During the transport through the decontamination heating screw 2, which is operated with thermal oil, the temperature increases from room temperature T1 to the process temperature T2, where the process temperature is 150° C. The flakes here crystallize sufficiently so that they can be transported without problem and are not sticky.

After heating the flakes to the process temperature, they are introduced into the decontamination reactor 3, which presents a conical shape broadening in the direction of gravity. There, the decontamination of the flakes starts immediately. Once the filling height in the decontamination reactor 3 is reached, the flakes continue to be transported at the same rate through the flake metering device 4 into the SSP heating screw 5, where they are moved from the decontamination heating screw 2 into the decontamination reactor 3. As a result, the filling level in this continuous operating procedure always remains at an optimal level. The process is regulated here in such a way that the residence time of the flake in the decontamination reactor 3 can no longer fall below the minimum residence time.

The temperature T3 in the decontamination reactor 3 is 150° C. The crystallization or decontamination of the flakes is carried out as a function of the two factors, time and temperature. The air feed, by means of which the contaminants expelled from the flakes are removed, is a supporting characteristic of this process. The air is heated to the process temperature T3, and introduced by means of the air feed 11 into the decontamination reactor 3, it flows through the flakes located in the decontamination reactor 3, and it is moved out by means of the air removal device 12. The flow rate of the air must not fall below a minimum value, and in the process it is set so that the flakes do not become turbulent. The only purpose of the air stream is to remove the contaminants expelled from the flakes more easily and more rapidly. The air presents substantially a temperature in the range of the process temperature. In the decontamination reactor 3, no heating of the flakes thus occurs, but only a stabilization of the temperature at the process temperature.

Because the transfer of the flakes from the decontamination reactor 3 into the flake metering device 4 and into the SSP heating screw 5 is optimally insulated, and thus there is no heat loss, or as little heat loss as possible, the flakes present a temperature T4 of 150° C. at the beginning of the SSP heating screw 5 which conveys the flakes into the SSP reactor 6. In the SSP heating screw 5, which is operated with thermal oil, the flakes are heated from 150° C. (T4) to 190° C. (T5).

To optimize the process control with regard to the IV of the flakes, the intrinsic viscosity of the flakes is determined automatically by an IV measurement device 14 which is located on the SSP reactor, after or during the filling process. Using this measurement value, the residence time of the flakes in the SSP reactor 6 is determined.

To facilitate the further removal of contaminants and the increase of the intrinsic viscosity, a vacuum is applied to the SSP reactor 6, which is substantially cylindrical in shape, with a gas pressure of 1 millibar using a vacuum pump 9. To improve the removal of the contaminants, nitrogen or carbon dioxide is supplied through an inert gas inlet 15, and it flows around the flakes in such a way that they do not become turbulent. The inert gas enriched with contaminant is removed by suction through the vacuum pump 9. The temperature T6 in the SSP reactor 6 is 190° C.

After half of the originally calculated residence time of the flakes in the SSP reactor 6 has elapsed, a sample of the flake is analyzed again with the IV measurement device 14 to determine the value of the intrinsic viscosity. Due to the changes in the IV of the flake, the remaining residence time in the SSP reactor 6 can be controlled or corrected. Based on the two measurements of the IV during the SSP treatment, an optimal process result with regard to intrinsic viscosity can be achieved.

After the treatment in the SSP reactor 6, the flakes are introduced into a flake metering device 7, from which they are fed by metering into the cooling reactor 8. In the flake metering device 7, the flakes present a temperature T7 of approximately 190° C., which is the temperature of the SSP process. The cooling of the flakes in the cooling reactor 8 to a temperature T8 of approximately 70° C. is carried out by means of environmental air. The cooling must occur so rapidly that, in spite of the humidity contained in the environmental air, no hydrolysis of the flakes takes place.

Figure 2:
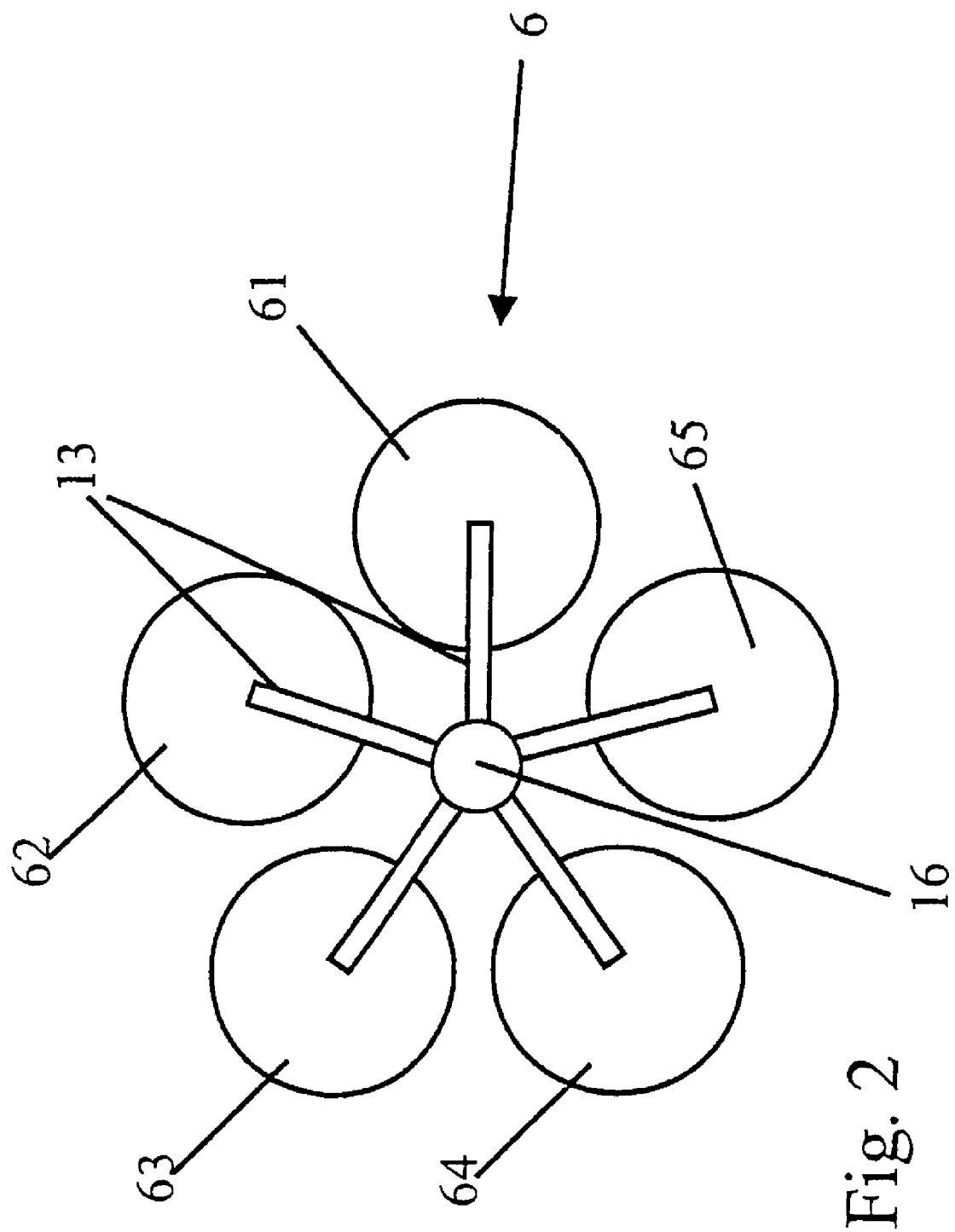
FIG. 2 shows a schematic representation of a top view of an SSP reactor unit.

FIG. 2 shows a special design of the SSP reactor 6. Here five, substantially cylindrically, individual SSP reactors 61, 62, 63, 64 and 65 are arranged in a circular structure to form an overall SSP reactor 6. After heating the flakes from T4 to T5 (150° C. to 190° C.) in the SSP heating screw 5, they are distributed in a controlled manner into the individual reactors through a distribution funnel 16 and distribution ducts 13.

The flakes are directed, for example, by the distribution funnel 16 through a distribution duct 13 into the individual SSP reactor 61 until the latter has reached the process filling height. While, in the individual SSP reactor 61, the SSP process starts with the measurement of the IV by the IV measurement device 14, the flakes which continue to be continuously conveyed by the SSP heating screw are led through the distribution funnel 16 and the distribution duct 13 into the individual SSP reactor 62, until the production filling height is reached. While the SSP process in the individual SSP reactor 62 now starts with a measurement of the IV of the flakes, the individual SSP reactor 63 is filled with heated flakes. In this way, the individual SSP reactors 61-65 are filled successively with flakes.

Until the individual SSP reactor 65 is filled with flakes, the SSP process in the individual SSP reactor 61 is completed, and the flakes are removed through the flake metering device 7 in the direction towards the cooling reactor 8. Therefore, the individual SSP reactor 61 can also be filled again after the individual SSP reactor 65 has been filled. In this way, the SSP process, which is preferably carried out batch-wise, can be run as a nearly continuous process with continuous flake feed from the SSP heating screw 5 and with continuous flake removal by the flake metering device 7 into the cooling reactor 8.

What is claimed is:

1. A method for preparing plastics that are contaminated and ground into flakes, comprising at least a decontamination step and a SSP treatment step performed on the flakes, each taking place in at least one reactor and the SSP treatment being adiabatic, wherein the decontamination of the flakes is carried out in at least one decontamination reactor and the SSP treatment of the flakes is carried out in at least one SSP reactor, wherein a SSP process temperature of the flakes in the SSP reactor is higher than a decontamination process temperature of the flakes in the decontamination reactor, and wherein heating the flakes to the SSP process temperature occurs while the flakes are located outside of the SSP reactor.

2. The method according to claim 1, and wherein no mechanical energy is added to the material to be prepared in the SSP reactor.

3. The method according to claim 1 further comprising a hot gas that flows around the material to be prepared in the decontamination reactor.

4. The method according to claim 3, wherein the hot gas that flows around the material to be prepared is air.

5. The method according to claim 1, wherein the decontamination of the flakes takes place continuously in the decontamination reactor.

6. The method according to claim 1, wherein, in the decontamination reactor, the temperature is in the range from approximately 20° to 200° C.

7. The method according to claim 1, wherein the heating of the material to be prepared to the decontamination process temperature occurs continuously before the decontamination reactor.

8. The method according to claim 7, wherein the heating occurs in one of a heating screw or in a vibrating helical conveyor.

9. The method according to claim 8, wherein thermal oil is used as medium for transferring heat to the material to be prepared.

10. The method according to claim 1, wherein the SSP treatment in the SSP reactor is carried out in batches.

11. The method according to claim 1, wherein low pressure conditions exist in the SSP reactor.

12. The method according to claim 11, wherein, in the SSP reactor, a vacuum is present with a gas pressure of at most 100 mbar.

13. The method according to claim 1, and wherein the SSP process temperature is in the range from approximately 150° to 250° C.

14. The method according to claim 1, wherein the temperature increase of the material to the SSP process temperature occurs continuously before the entry into the SSP reactor.

15. The method according to claim 14, wherein the temperature increase to the SSP process temperature occurs in one of a heating screw or in a vibrating helical conveyor.

16. The method according to claim 14, wherein thermal oil is used as medium for transferring heat to the material to be prepared.

17. The method according to claim 1, wherein the SSP process is carried out under a protective gas atmosphere.

18. The method according to claim 1, wherein a gas stream is led through the material to be prepared, which removes at least one of degradation products, contaminants, and ultrafine particles from the SSP reactor.

19. The method according to claim 1, wherein the IV of the material to be prepared is determined at least once before or during the preparation process.

20. The method according to claim 19, wherein the result of the IV determination determines at least parts of the process course.

21. The method according to claim 1, and carrying out a measurement of the IV before the entry of the material to be prepared into the SSP reactor, and, based on its results, determining a residence time of the material in the reactor.

22. The method according to claim 20, further comprising carrying out an additional measurement of the IV after substantially half of the determined residence time of the material to be prepared in the SSP reactor, and, based on the results thereof, controlling the previously determined residence time in the SSP reactor.

23. The method according to claim 1, further comprising cooling the material to be prepared, after the residence time in the SSP reactor, to a temperature below the glass transition point.

24. The method according to claim 23, wherein the cooling is carried out in one of a cooling screw, a vibrating helical conveyor, or in a fluidized bed reactor.

25. The method according to claim 23, wherein the cooling is carried out by means of environmental air.

26. The methoding according to claim 1, wherein the contaminated plastics ground into flakes comprise post-consumer plastics.

27. The methoding according to claim 1, wherein the contaminated plastics ground into flakes comprise RPET.

28. The methoding according to claim 1, wherein the IV of the material to be prepared is determined at least once before or during the preparation process.

29. A method for preparing plastic flakes, the method comprising:
   heating the plastic flakes to a first process temperature prior to delivering the plastic flakes to a decontamination reactor;
   decontaminating the plastic flakes in the decontamination reactor without heating the flakes beyond the first process temperature;
   heating the plastic flakes to a second process temperature at a location outside of the decontamination reactor after decontaminating the plastic flakes in the decontamination reactor and prior to delivering the plastic flakes to an SSP reactor, the second process temperature greater than the first process temperature; and
   decontaminating the plastic flakes in the SSP reactor without heating the plastic flakes beyond the second process temperature.

* * * * *

UNITED STATES PATENT AND TRADEMARK OFFICE
CERTIFICATE OF CORRECTION

PATENT NO. : 8,394,866 B2  
APPLICATION NO. : 11/886986  
DATED : March 12, 2013  
INVENTOR(S) : Friedlaender et al.

Page 1 of 1

It is certified that error appears in the above-identified patent and that said Letters Patent is hereby corrected as shown below:

On the Title Page, Item (58), under "Field of Classification Search", in Column 1, Line 4, delete "131," and insert -- 422/131, --, therefor.

In the Claims

In Column 10, Line 27, in Claim 26, delete "methoding" and insert -- method --, therefor.

In Column 10, Line 30, in Claim 27, delete "methoding" and insert -- method --, therefor.

In Column 10, Line 32, in Claim 28, delete "methoding" and insert -- method --, therefor.

Signed and Sealed this  
Ninth Day of December, 2014

Michelle K. Lee  
*Deputy Director of the United States Patent and Trademark Office*

UNITED STATES PATENT AND TRADEMARK OFFICE
CERTIFICATE OF CORRECTION

PATENT NO.       : 8,394,866 B2
APPLICATION NO.  : 11/886986
DATED            : March 12, 2013
INVENTOR(S)      : Friedlaender et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this
First Day of September, 2015

Michelle K. Lee
*Director of the United States Patent and Trademark Office*